United States Patent [19]

Yamaguchi

[11] Patent Number: 4,787,052
[45] Date of Patent: Nov. 22, 1988

[54] MOISTURE MEASURING METER OF A HYDROUS SUBSTANCE

[75] Inventor: Tetsuo Yamaguchi, Chiba, Japan

[73] Assignees: Kabushiki Kaisha Toyoko Elmes, Yokohama; Fukken Chosa Sekkei Kabushiki Kaisha, Hiroshima, both of Japan

[21] Appl. No.: 858,629

[22] Filed: May 2, 1986

[30] Foreign Application Priority Data

May 2, 1985 [JP] Japan ................... 60-93912

[51] Int. Cl.[4] .................. G01N 5/02; G01N 25/56
[52] U.S. Cl. ..................... 364/550; 177/25; 73/29; 73/76; 364/567
[58] Field of Search ............ 364/497, 550, 551, 556, 364/567, 496; 73/29, 73, 76; 131/299, 303; 177/25, 164, 165, 25.11, 25.12, 25.18, 25.19; 324/58.5 A, 161; 436/30; 219/10.55 R

[56] References Cited

U.S. PATENT DOCUMENTS

| | | | |
|---|---|---|---|
| 4,193,116 | 3/1980 | Funk | 364/556 |
| 4,316,384 | 2/1982 | Pommer et al. | 73/76 |
| 4,485,284 | 11/1984 | Pakulis | 219/10.55 R |
| 4,513,759 | 4/1985 | Wochnowski et al. | 131/303 |
| 4,554,132 | 11/1985 | Collins | 73/76 X |
| 4,651,556 | 3/1987 | Seaman | 73/73 X |
| 4,666,007 | 5/1987 | Knothe et al. | 73/76 |

Primary Examiner—Parshotam S. Lall
Assistant Examiner—Joseph L. Dixon
Attorney, Agent, or Firm—Armstrong, Nikaido, Marmelstein & Kubovcik

[57] ABSTRACT

A method for measuring the moisture content of a hydrous material employs the steps of determining the tare weight of a shallow rectangular sample container having a top, adding a sample to the container, weighing the sample and container, applying heat and pressure to the sample container using a pair of aluminum or graphite blocks, weighing the sample after heating, and calculating the moisture content. The method is applicable to measurements which are made outside the laboratory.

3 Claims, 2 Drawing Sheets

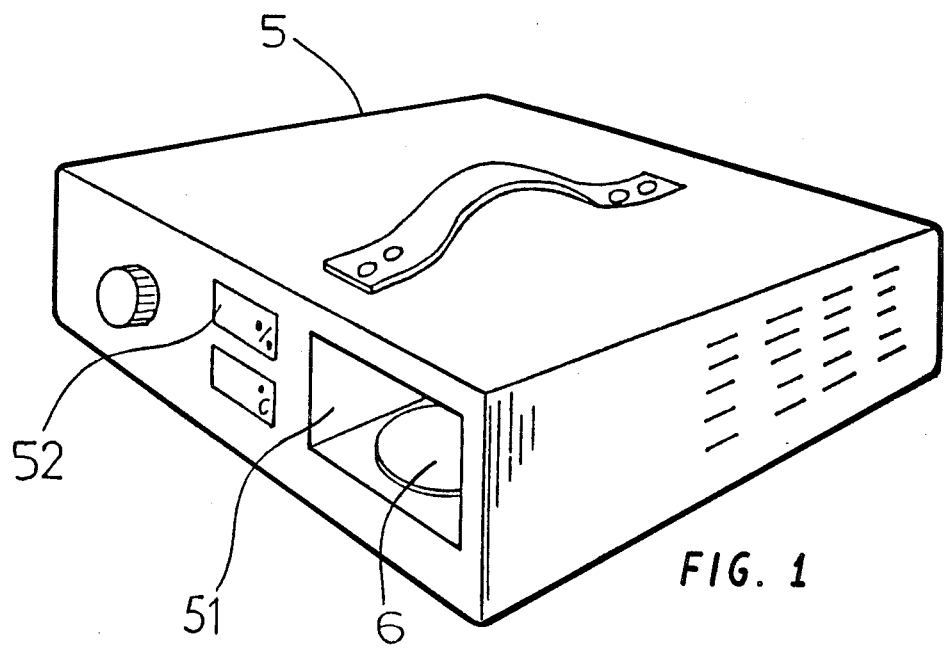
FIG. 1
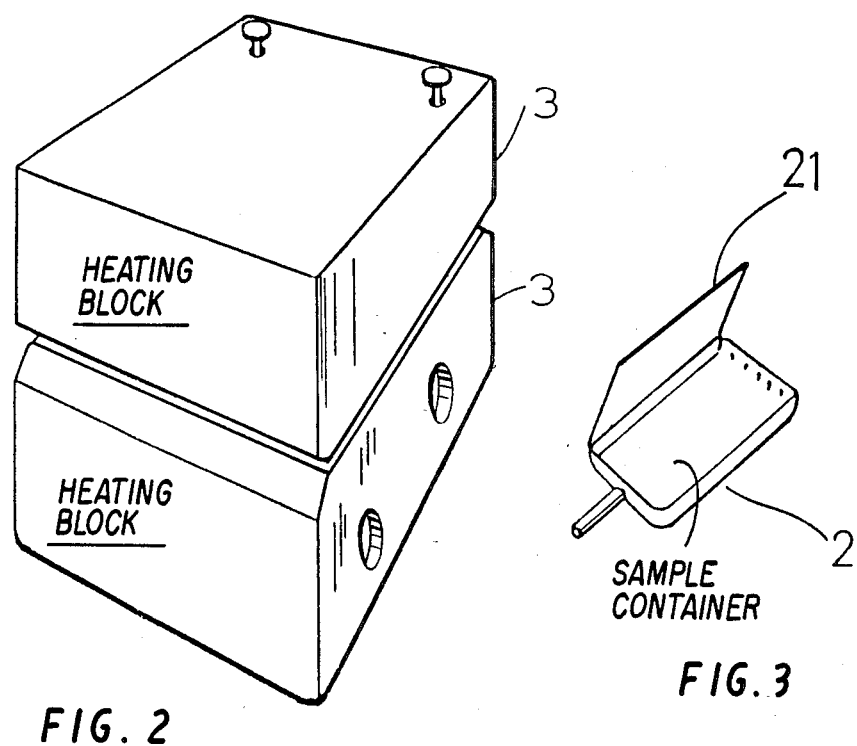
FIG. 2
FIG. 3

MOISTURE MEASURING METER OF A HYDROUS SUBSTANCE

BACKGROUND OF THE INVENTION

The precise measurement of the moisture content of a material is important in engineering and also in industries dealing with food, cosmetics, tobacco and metal castings, to name a few.

Measurements in the field are often valuable in civil engineering such as in the measurement of the moisture content of ground soil prior to preparing the land for a road.

Among the known methods for the measurement of moisture content are those which involve heating of the sample using a frying pan, a microwave oven or an infrared heater. Soil may be burned by first impregnating the soil with alcohol, igniting the sample, and measuring the weight difference in weight before and after this process. Neutron bombardment of hydrated soil allows calculation of the quantity of water molecules present because water molecules appear on the circumferential surface after neutron bombardment.

The prior art methods for the measurement of moisture content have several known problems which limit their usefulness. Heating according to Japanese Industrial Standards requires a total of 8 hours and alternative standard methods require heating for at least 15-20 minutes. These time frames are impractical if they are to be used at the site of sample collection.

If the temperature is raised above that specified in the standard methods, the temperature may be high enough to cause decomposition of the organic matter which is present in many samples, resulting in the formation of additional water and of oxide compounds. The loss of water and the formation of heavier derivative material results in an inaccurate measurement.

When a burner is used to directly heat the substance, localized overhydration and underhydration of the material is known to occur.

Microwave ovens are not a practical alternative to the direct application of heat because, as the material dries, the cavity no longer contains sufficient amounts of water to absorb the radiation and the "empty-frying" of the sample results in early failure of the equipment.

SUMMARY OF THE INVENTION

This invention relates to a method for the measurement of the percentage content of a hydrated substance by calculating the difference between the weight of the material in the hydrated condition and the weight of the material which is absolutely dry. In the practice of this invention, a large heating medium, with a high specific heat capacity, is used both to heat the sample material and to pressurize the sample material to obtain an absolutely dry condition.

The method further provides a means for weighing the sample material before and after heating and for calculating the percentage of moisture content of the substance.

This method is applicable to civil engineering, food handling, ceramics, tobacco processing, casting processes and other operations in which it is necessary to determine rapidly and precisely the amount of moisture which is present.

BRIEF DESCRIPTION OF THE DRAWINGS

FIG. 1 is an external view of the electric balance and moisture meter according to this invention.

FIG. 2 is an external view of the heating blocks employed in this invention.

FIG. 3 is a sample container for use in this invention.

DETAILED DESCRIPTION OF THE INVENTION

Figure 4:
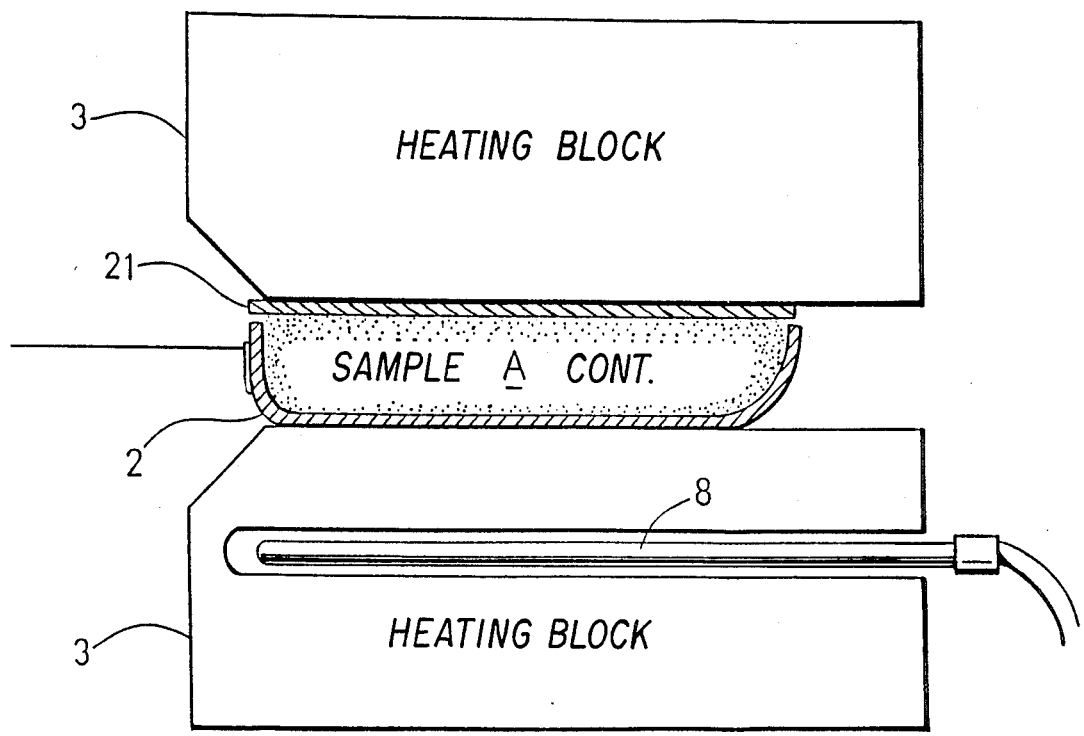
FIG. 4 is a cross section of the heating blocks having a sample holder and sample pressed between heating blocks.

Applicants' invention may be summarized as follows:

Step (a) A sample collector is weighed using an electronic balance and the weight is stored in the memory of a computer associated with the electronic balance.

Step (b) A sample is introduced into the sample container, the container and sample are weighed, and the results stored in the memory of the computer associated with the electronic balance.

Step (c) The sample container is inserted between heating blocks and the blocks are pressed together on the top and bottom of the sample container.

Step (d) The sample is removed from the heating blocks and weighed, and the result is entered into the memory of the computer associated with the electronic balance.

The computer calculates the water content percentage of the sample based upon the weight of the sample container, the weight of the hydrated sample, and the weight of the dried sample, and displays the result.

If it is necessary to confirm the result, the sample may be reheated and reweighed to assure that all moisture has been removed.

The material container of this invention is illustrated in FIG. 3. The container consists of a shallow rectangular box 2 having a top covering 21. In the preferred embodiment, this container is formed from heat conductive aluminum plates. The material container may be equipped with a heat sensor to measure the temperature of the sample and the temperature may be displayed on the face of the moisture measuring instrument 5.

The heating blocks are illustrated in FIG. 2. The blocks have facing sides having a very smooth finish and the corners are beveled on one side to facilitate the insertion of the material container between the imposing faces. The material of which the blocks are formed has superior heat conduction and a high heat capacity, and it is preferable to use aluminum, graphite, or other materials which have a high heat capacity. Alternative heating units which employ expandable, air-tight containers enclosed within liquified heating media are also suitable.

The heating blocks may contain a heating element 8, which can be turned on and off under the control of a thermostat to heat the blocks to a desired temperature and to maintain them at that temperature.

Lagging materials may be used as a coating on the heating blocks for field use. The principal benefit derived from coating the blocks is to prevent rapid drop in temperature of the blocks when they are being transported from one point to another at an operational site.

The measuring instrument used in this invention performs the functions of weighing, calculating, and displaying the result on a meter or digital readout. The instrument 5 has an opening 51 on the front equipped with an electronic scale. Within the instrument is a microcomputer with a memory capacity. The weight of the sample weighed on the electronic scale 6 at the end of each step is loaded into the memory and the computer performs the calculation of the moisture content of the sample based upon those weights.

For this computation, the computer performs the following calculation:

$$M = \frac{W - W_o}{W} \times 100$$

where W equals the weight of sample A in the hydrous state and Wo is the weight of the sample in the dehydrated state.

The result is preferedly indicated by a digital display 52 indicating the moisture content, and the result may also be printed from an output signal.

A portable battery, such as a dry cell battery, may be used as a power source for the instrument, or the instrument may be adapted to operate using ca. 100-110 volt alternating current.

The determination of moisture content is performed as follows. First, the weight of the empty container is determined on the electronic scale and the weight is entered into the microcomputer memory. Then, a fixed amount of sample, typically gathered at the operation site, is placed in the container and the gross weight of the material and container is measured on the electronic scale and entered into the microcomputer.

The heating blocks are heated to a preset temperature, typically 200° C., and maintained at that temperature if possible. The high heat capacity of the blocks prevents rapid change in temperature. If an adequate source of electricity is not available at the operational site, a simple gas burner may be used to heat the blocks, particularly when analyzing very moist substances.

The container with enclosed sample is inserted between the heated blocks, as illustrated in FIG. 4, and the blocks are pressed against the top and bottom surfaces of the sample container. Because the sample is pressed and heated evenly throughout, the dehydration step requires a minimum amount of time. The temperature of the material in the container may be used to monitor the progress of drying.

In contrast to the prior art method, this new method uses heating blocks having a high heat capacity and it is possible to obtain a dry sample, in most cases, even when a source of heat is not available at the operational site and the blocks must be preheated elsewhere. Since the sample is heated evenly throughout, a minimum amount of time is required to obtain a dry sample.

After heating, the container and sample are weighed on the electronic scale, the weight input to the microcomputer, which then calculates the moisture content. This calculation is based upon the gross weights of the sample prior to and after dehydration and the tare weight of the container. The result is displayed on meter 52.

The advantages of this invention are as follows:

(I) The power source of the instrument can be a portable battery. The heating blocks may be heated in advance prior to going to the operational site, thus obviating the need for additional power at the site of measurement.

(II) Heating of the sample is accomplished quickly and thoroughly, because the surface of the heating blocks is flat and smooth and because the weight of the heating blocks covering the top and bottom of the container presses the sample as it is being heating. As a result, the samples can be heated quickly to 200° C. without decomposition or burning of organic matter in the sample.

(III) The cost of manufacturing the moisture measuring instrument is lower than the prior art devices and transportation is facilitated by the simple structure.

(IV) The moisture content of substances other than soil may also be determined by this method.

I claim:

1. A method for measuring the moisture content of a hydrous material comprising: determining the tare weight of a shallow rectangular sample container having a top; adding a sample of material to the sample container; weighing the sample and sample container; applying heat and pressure to said sample container by means of a heating medium comprising a pair of blocks formed from a material selected from the group consisting of aluminum and graphite; weighing the sample after heating; and calculating the percentage moisture content M according to formula I $$M = \frac{W - W_o}{W} \times 100 \qquad (I)$$

wherein W is the weight of the sample in the hydrous state and Wo is the weight of the sample in the dehydrated state.

2. A method according to claim 1 wherein said heating medium is pre-heated before heating and pressurizing the sample.

3. A method according to claim 1 wherein said material container is placed between faces of said heating medium.

* * * * *